United States Patent
Brown, Jr. et al.

[11] Patent Number: 6,099,509
[45] Date of Patent: Aug. 8, 2000

[54] DISPOSABLE KIT FOR SECURING AN I.V. CATHETER

[76] Inventors: William S. Brown, Jr.; Benjamin C. Brown, both of 217 Shadybrook La., Mt. Sterling, Ky. 40353

[21] Appl. No.: 09/295,486

[22] Filed: Apr. 20, 1999

Related U.S. Application Data

[60] Provisional application No. 60/102,015, Sep. 28, 1998.

[51] Int. Cl.⁷ ..................................................... A61M 5/32
[52] U.S. Cl. ........................... 604/180; 604/174; 602/41; 602/43
[58] Field of Search ..................... 604/174, 180; 128/DIG. 26, 6; 602/41, 43, 52, 54

[56] References Cited

U.S. PATENT DOCUMENTS

| | | |
|---|---|---|
| 2,821,194 | 1/1958 | Simmons . |
| 3,357,425 | 12/1967 | Morgan . |
| 3,585,996 | 6/1971 | Reynolds et al. . |
| 3,834,380 | 9/1974 | Boyd . |
| 4,170,993 | 10/1979 | Alvarez . |
| 4,460,356 | 7/1984 | Moseley . |
| 4,484,914 | 11/1984 | Brown . |
| 4,669,458 | 6/1987 | Abraham et al. . |
| 4,698,057 | 10/1987 | Joishy . |
| 4,704,177 | 11/1987 | Vaillancourt ............................ 156/226 |
| 4,822,342 | 4/1989 | Brawner . |
| 4,875,896 | 10/1989 | Kurtz ....................................... 604/187 |
| 4,976,700 | 12/1990 | Tollini . |
| 5,160,315 | 11/1992 | Heinecke et al. .......................... 602/57 |
| 5,215,532 | 6/1993 | Atkinson . |
| 5,520,629 | 5/1996 | Heinecke et al. .......................... 602/57 |
| 5,546,938 | 8/1996 | McKenzie . |
| 5,562,211 | 10/1996 | Simons et al. . |

Primary Examiner—Wynn Wood Coggins
Assistant Examiner—Eric Klein
Attorney, Agent, or Firm—Wood, Herron & Evans LLP

[57] ABSTRACT

A kit for disposing of a contaminated I.V. needle and delivering adhesive wound dressings to a patient with preferably a single gloved hand includes an adhesive mounting substrate to attach the apparatus to an available surface. An adhesive needle sheath carrier extends from the base of the apparatus for securing a needle and needle sheath for disposal following use. To the base of the apparatus are releasably adhered a wound barrier and taping strips to aid in securing a catheter to a patient. Tabs are provided on the wound barrier and taping strips to facilitate their removal from the base of the apparatus. The apparatus allows a medical technician to insert a catheter into a patient and maintain pressure on the catheter at the wound site with one hand, while disposing of the contaminated needle and then securing the catheter with wound dressings, all with preferably a single gloved other hand, thereby reducing the incidence of infection or injury.

65 Claims, 7 Drawing Sheets

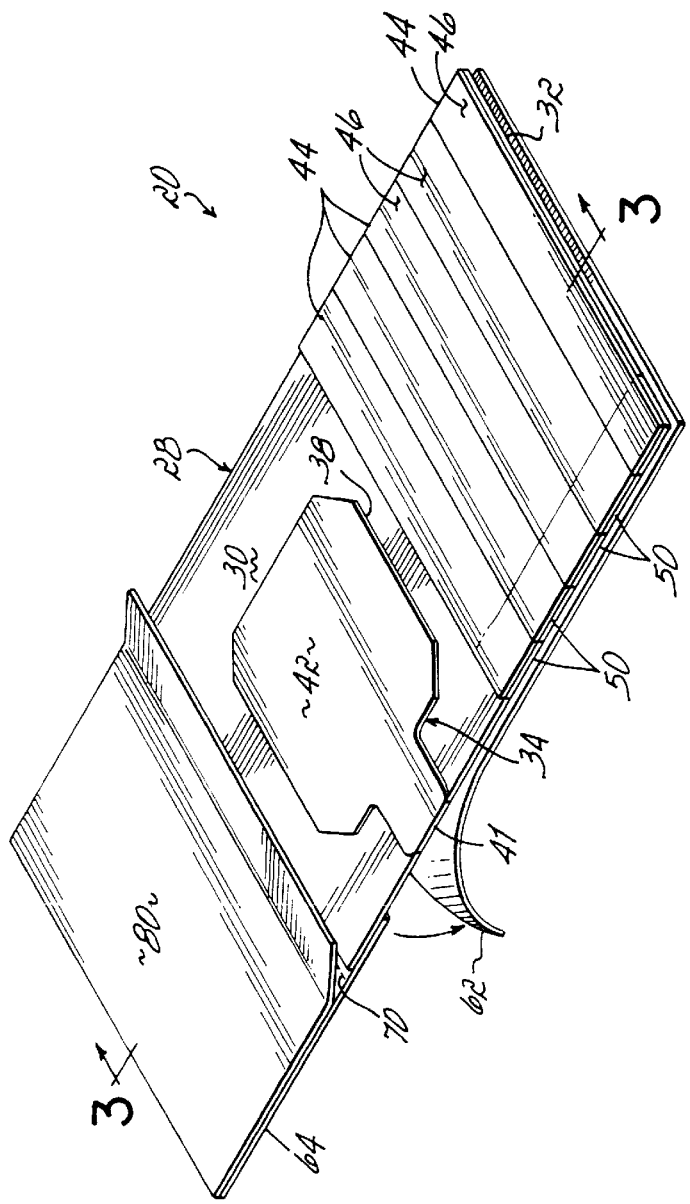
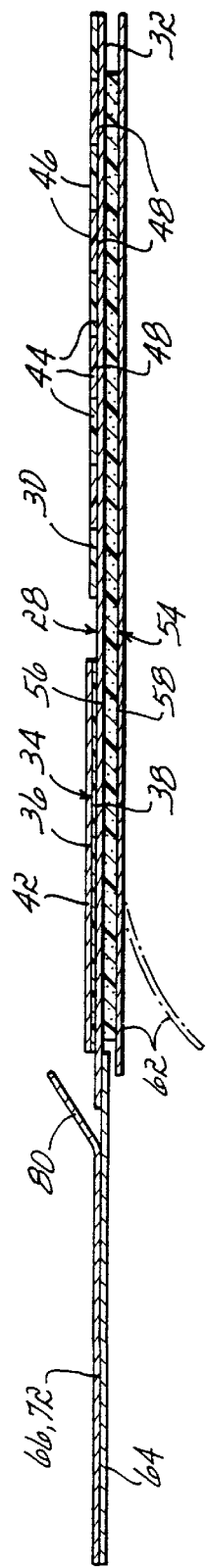

DISPOSABLE KIT FOR SECURING AN I.V. CATHETER

CROSS-REFERENCE TO RELATED APPLICATIONS

This application claims priority to Provisional Patent Application, Ser. No. 60/102,015, filed on Sep. 28, 1998, entitled ONE ARM NURSE which is fully incorporated by reference herein.

FIELD OF THE INVENTION

The present invention relates generally to a taping kit and needle disposal apparatus, and more specifically to a kit which reduces the risks of contamination, infection and injury during I.V. insertion and needle disposal procedures. The kit facilitates secure application of a catheter by a medical technician to a site on a patient and disposal of a contaminated I.V. needle, all with a preferably single gloved hand.

BACKGROUND OF THE INVENTION

In a typical I.V. catheter insertion procedure, the I.V. catheter is inserted into a patient after preparation and sterilization of the insertion or wound site. Thereafter, the catheter is held in place by a plurality of tapes which are typically torn from a roll of surgical tape. The first tape is typically or preferably twisted around the catheter in a butterfly-like fashion and subsequent strips are then torn from the roll and applied to the ends of the butterfly tape and over the catheter to hold it in place. Often, an adhesive patch, or wound barrier, is applied directly over the catheter, with tape strips subsequently used to additionally secure the catheter. This typical procedure has a number of disadvantages.

Since the tape is not applied until after the catheter is inserted into the vein and, since the tape is typically torn from tape rolls, it is clear that the technician must frequently let go or release the catheter so that both hands can be used for the taping operation. This catheter release is required to either tear the strips from the roll of tape or, in the alternative, for the removal of pre-torn strips and their placement around the catheter. Any time the catheter is released after it has been inserted, it is in danger of falling out, thus requiring a reinsertion, at the least.

In one typical mode of operation then, a technician will tear off a number of tape strips and place them on the bed rail, on the bedside cabinet, or some other structure. These surfaces are mostly non-sterile. After the insertion of the catheter, the technician still must use two hands in forming the strip around the catheter, particularly where a butterfly wrap is used, and the catheter is then in danger of falling out when not held in place during the use of both hands to handle the tape. The use of both hands in tearing off the tape and placing it on a non-sterile surface introduces the possibility of contamination of the underside of the tape, resulting in a non-sterile application. Moreover, because the tape must be torn and because it is much easier to tear the tape with an ungloved hand, frequently technicians will carry out at least this part of the procedure without using gloves at all. Use of bare or ungloved hands presents contamination problems to both patients and technicians. Additionally, potential contamination may arise from placing tape strips on non-sterile surfaces such as bed rails or cabinets just prior to their application to the patient.

A second problem that arises from this typical method, apart from the problems incurred with taping, concerns needle disposal. Following the insertion of an I.V. catheter into a patient, the needle used for the catheter insertion is removed, leaving the catheter in the patient's vein. The technician involved in inserting the catheter must now dispose of a contaminated needle, all the while maintaining pressure on the I.V. wound site so the catheter does not become loose and/or fall out before taping. This increases the difficulty of disposal of the needle, and often results in the contaminated needle being placed on a table tray or other surface near the area where the technician is at work securing the catheter. There, it has the potential to inadvertently puncture and infect other persons such as hospital personnel, the patient, family members or others. This also increases the chances that the contaminated needle may be lost prior to disposal and therefore pose an ongoing risk to other persons. Since the technician cannot usually release pressure on the catheter to take the needle to a disposal unit (which may be across the room or the like), disposal of the needle may be effected by bringing a disposal unit to the technician. This results in a disposal unit containing several contaminated articles being brought into close proximity with the patient, and is undesirable.

Another problem with the typical method of reinserting the needle in the protection sheath prior to its disposal is that the technician must hold the sheath in one hand while placing the used needle inside with the other hand. This brings the needle into very close proximity with the skin of the sheath-holding hand of the technician and constitutes risk of an inadvertent "stick" or puncture with a contaminated needle. All of the above problems increase the opportunities for either patient, technician or others to become infected. It has been estimated that each year, almost two million individuals who enter hospitals in this country acquire infections they did not have when they went there, and of these, eighty thousand die. (Jeffrey A. Fisher, *The Plague Makers;* NY: Simon & Schuster, 1994).

Accordingly, and in view of the above background, there is a need for a sterile I.V. catheter securing system and/or for a needle disposal system which overcomes at least some of the problems noted above. It is also desirable to provide a system to facilitate the sterile handling of sterile wound barriers and tape strips. It is also desirable to provide a system which allows for the safe disposal of contaminated needles.

SUMMARY OF THE INVENTION

This invention solves the heretofore mentioned problems and perhaps others associated with known methods and apparatuses used for dressing I.V. wound sites by the provision of a kit having components which can be completely manipulated preferably with one hand so that it is not necessary for the technician to release his hold of the catheter once it has been inserted into a vein. At the same time, the kit provides for easy grasping of a sterile wound barrier, which is an adhesive patch used to cover the wound site, and sterile tape strips used to hold the catheter in place, preferably with a single gloved hand, while the other hand is continually uninterruptedly used to hold the catheter. Additionally, the technician may safely dispose of the contaminated catheter needle with the same operative hand while maintaining pressure on the I.V. wound site with the other and thus not exposing it to the contaminated needle tip and an accidental "stick."

In one embodiment, the kit invention comprises a base and carrier sheet, on the top of which are mounted a number of removable adhesive tapes One of these is a patch referred to as a wound barrier for holding the catheter in place over the wound site. The remaining tapes are strips sized to be wrapped around the catheter or to otherwise hold it in place. In one embodiment, the wound barrier and the strips each may have a non-adhesive and/or raised tab for the purpose of easy grasping by a single gloved hand, so that each of the strips on the top of the carrier sheet can be easily removed from the base of the unit with a preferably single gloved hand while the base remains secured near the site by virtue of adhesive on its rear side.

The bottom of the base is provided with a mounting substrate, which includes an adhesive patterned on the underside of the base carrier for securing the entire unit to a nearby surface. In use, a removable backing releasably applied to the mounting substrate to protect the adhesive is removed.

Moreover the apparatus is provided in this embodiment with a relatively stiff adhesive sheath carrier attached to the base and covered by a releasable liner which is removed so the needle sheath can be attached to the unit as will be discussed.

In use, the kit would preferably be distributed in a sterile package or overwrap, also including an antibacterial wipe, etc. and removed from its package and the removable backing or liner on the underside of the mounting substrate is removed. The exposed mounting adhesive is then applied to any convenient surface near the procedure, for example, to the bedclothes, sheets, bed rail, cabinet, or whatever else resides in the area so the kit is positively secured in place. Thereafter, the technician, with gloved hands, can continue with the use of the kit to retrieve the catheter, the sterilization of the site, and the procedure, as will be described.

Once the needle/catheter has been inserted, the kit provides for safe, one-handed disposal of the contaminated needle while the technician maintains pressure on the I.V. wound site with the other hand prior to dressing the wound site. Specifically, after the I.V. catheter with needle has been inserted into the patient, the needle is extracted, leaving the catheter in the vein. As developed in the background of the invention the technician now has one hand on the catheter and the used or contaminated needle in the other. The needle must be disposed of with one hand while maintaining pressure on the I.V. wound site with the other hand so the catheter does not become loose and/or slip out of the patient.

This problem of needle disposal is solved by the kit of the present invention. Prior to insertion of the needle and catheter into the patient, the sheath used for housing the needle is placed on an adhesive sheath carrier of the kit. One side of the adhesive sheath carrier is then folded over the top of the sheath to secure it to the apparatus. The needle and catheter are then inserted into the patient. After the needle has been extracted from the patient, the technician may keep pressure on the I.V. wound site with one hand while using the other hand to reinsert the contaminated needle into its sheath, which is adhered to the adhesive sheath carrier of the apparatus. At this point, it is not necessary to sturdy the base carrier with the other hand. As such, the technician's offhand is prevented from sustaining injury from a needle stick. After dressing the wound and securing the catheter with the wound barrier and tape strips, the entire remaining kit may be rolled up for disposal in a disposal unit. Alternately, the needle and needle sheath may be rolled up in the sheath holder and disposed in a disposal unit.

Following reinsertion of the needle into the sheath adhered to the adhesive sheath carrier, the technician is still holding the catheter in place with one hand while, at the same time, reaching to the kit and its strips with the other hand, where he or she removes the removable adhesive wound barrier and places it over the catheter surrounding the wound site. During this procedure, the technician can maintain control of the catheter by holding it in place with his other hand. The carrier layer, a stiffener of the wound barrier, can then be removed leaving a thin, clear, flexible, adhesive film over the wound site. Thereafter, the adhesive tape strips can be sequentially removed with one hand for further securing the wound barrier and the catheter as required. If necessary pressure can still be applied by the holding hand to the catheter or barrier.

This invention thus accomplishes several objectives. First, it eliminates the necessity to tear a number of strips from a roll of surgical tape, which is most easily done without gloves, despite the desirability of wearing gloves during the whole process. Moreover, the tapes can be pre-cut to the proper size for the particular I.V. kit so that it is not necessary to tear the tapes lengthwise to get the appropriate width.

In addition, it is not necessary to preliminarily tear the tapes and then apply them to what may be an unsterile surface, such as a bed rail or cabinet or the like, just prior to the application of the tapes. Also, since the adhesive tapes are removable from the carrier sheet easily with a single gloved hand, the invention permits the technician to maintain positive control at all times over the catheter which has been inserted, so that inadvertent movements do not allow slippage of the catheter and require a further puncture. Thus, positive control is maintained over the entire process while minimizing contamination and contact of the site with contaminated materials.

Finally, it will be appreciated that the kit of the present invention allows for safe, one handed disposal of contaminated needles by a technician while maintaining pressure on the I.V. wound site prior to closing the site with the wound barrier and tape strips. This greatly reduces the time the needle is typically left out unprotected, and the possibility of infection of patient, hospital personnel, and others due to an inadvertent puncture by a contaminated needle. As a result of this increased safety of disposal, there is a corresponding reduction in the likelihood of illness or loss of life due to infection.

These and other objections and advantages will become readily apparent from the following written description of preferred alternative embodiments and from the drawings in which:

BRIEF DESCRIPTION OF THE DRAWINGS

FIG. 2 is a perspective view of the assembled kit of FIG. 1;

FIG. 3 is a cross-sectional view of the kit taken along lines 3—3 of FIG. 2;

DETAILED DESCRIPTION OF THE PREFERRED EMBODIMENT

Figure 1:
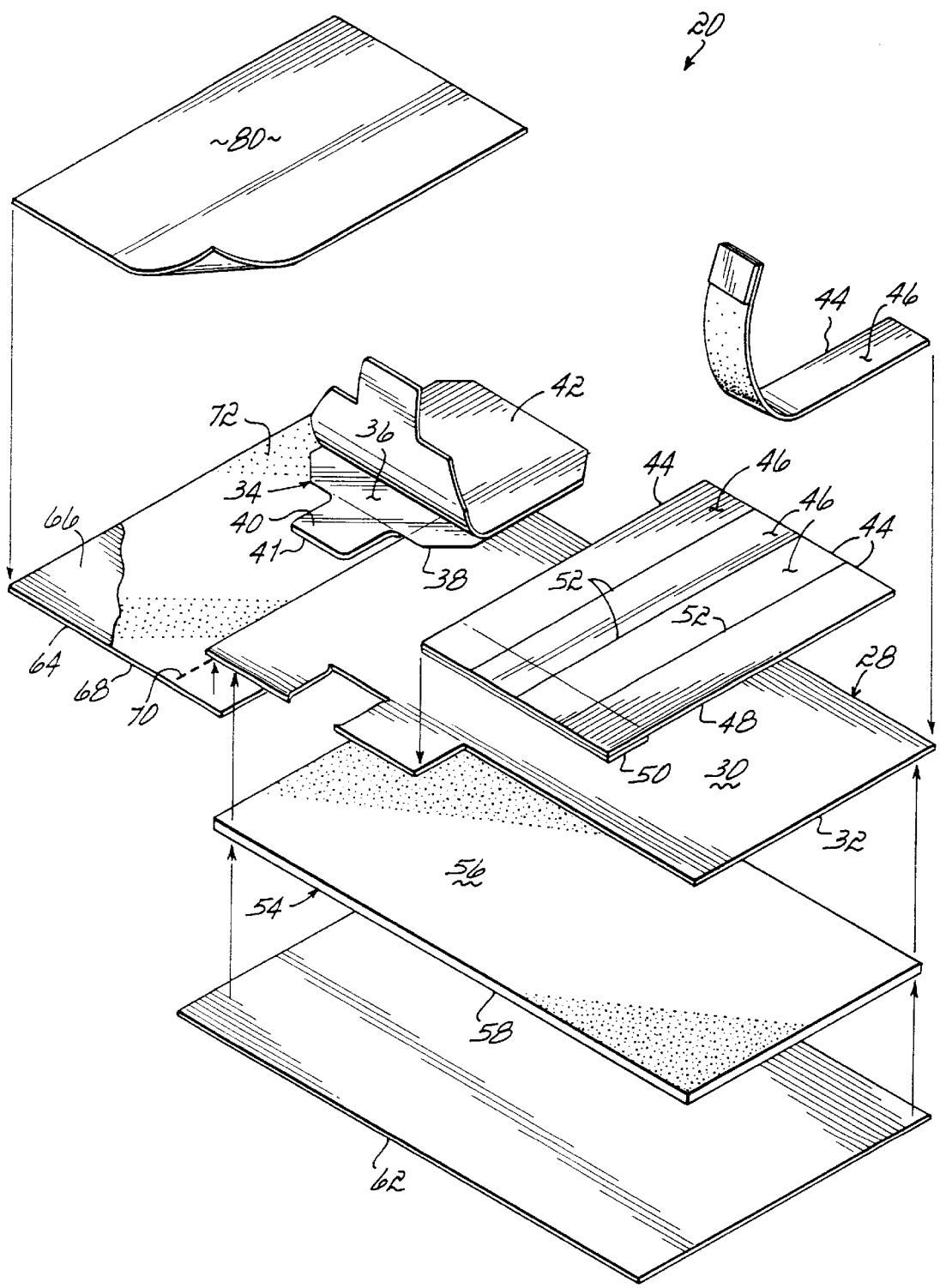
FIG. 1 is an exploded perspective view of a one embodiment of the kit according to the present invention.

The I.V. catheter securing and needle disposal kit or apparatus 20 in the embodiment as depicted in FIGS. 1–8 comprises a base carrier 28 used as a base sheet having top and bottom faces 30, 32. The top face 30 of the base carrier 28 is adapted to receive and carry wound dressings to be applied to a patient. The kit 20 includes an adhesive mounting substrate 54 which releasably adheres the apparatus to an available surface. The mounting substrate 54 has top and bottom faces wherein the top face 56 of the mounting substrate is attached to the bottom face 32 of the base 28. A removable backing or liner 62 is releasably adhered to the bottom face 58 of the mounting substrate 54, removal of which exposes an adhesive surface (such as a pressure sensitive adhesive) on the bottom face of the mounting substrate. The apparatus 20 further includes a sheath carrier 64 attached to the base 28 and extending therefrom. The sheath carrier 64 has top and bottom faces 66, 68. Disposed on the top face 66 of the sheath carrier 64 is an adhesive 72 (such as a foamed adhesive layer, a patterned adhesive or other adhesive) which facilitates one-handed disposal of a contaminated needle by providing an adhesive surface for carrying a sheath 26 of an I.V. needle 22. Prior to its use, the sheath carrier 64 with adhesive 72 includes a peel-away adhesive cover or liner 80 which is releasably adhered to the top face 66 of the sheath carrier.

Located on the top face 30 of the base 28 are mounted a number of wound dressings which comprise several removable adhesive tapes. In particular, one of these adhesive tapes is a patch referred to as a wound barrier film 34. The wound barrier 34 is used primarily to hold a catheter 24 in place at a wound site 82 (FIG. 7) on a patient. The wound barrier 34 has a top face 36 and a bottom face 38. A carrier 42 is releasably adhered to the top face 36 of the wound barrier 34 and is removable from the base 28 with the wound barrier. The bottom face 38 of the wound barrier 34 includes an adhesive surface to facilitate the adherence of the wound barrier to a patient.

The wound barrier 34 itself is extremely thin and malleable to allow it to conform to the skin surface of a patient even when the surface is moved. As the skin flexes, the wound barrier 34 accommodates movement but exhibits resiliency to continue to conform to the skin when the skin is returned to its unflexed position. This allows the patient to enjoy a wide range of motion without the increased possibility that the wound barrier 34 may become loose and the catheter 24 dislodge from the patient.

In the absence of a support layer or carrier 42, the thin wound barrier film 34 would fold upon and stick to itself when removed from the base 28 of the apparatus 20. The carrier 42 acts as a support layer to ensure that this does not occur prior to application of the wound barrier 34 to the patient. Rather, the relatively stiff substance of the carrier 42 keeps the film 34 widely extended over the wound site 82. Following application of the wound barrier 34 to the patient, the carrier layer 42 may be peeled away from the film layer of the wound barrier 34 and disposed of, thus leaving the wound barrier film 34 intact over the wound site 82 on the patient. The clear film of the wound barrier 34 allows a technician or other medical personnel to observe the wound site 82. Protruding from one side of the wound barrier 34 is a tab 40 which facilitates the removal of the wound barrier film from the base 28 of the apparatus 20. The shape of the wound barrier 34 with tab 40 is coterminous with the shape of the carrier 42. Adhered to the under side of the tab 40 of the wound barrier 34 is a base tab 41 (FIG. 6) cut from the base 28 of the apparatus 20. The base tab 41 is coterminous with the tab 40 of the wound barrier 34 and aids in removal of the wound barrier from the base 28.

The remaining wound dressings are adhesive tapes disposed on the top face 30 of the base 28 and these comprise a plurality of tape strips 44 sized to be wrapped around the catheter 24 to supplement the securing of the catheter. Each of the tape strips 44 include a top face 46 and an adhesive bottom face 48. The tape strips 44 also include a non-adhesive or raised tab 50 attached to the bottom face 48 of the tape strip 44 to facilitate their removal from the apparatus 20 with a single gloved hand. The tab 50 attached to the bottom face of the tape strips 44 is cut from the base 28 of the apparatus 20. Each of the tape strips 44 are separated from one another by continuous cut lines 52.

The mounting substrate 54, attached to the bottom face 32 of the base 28, facilitates securing the apparatus 20 to an available surface 60. The top face 56 of the mounting substrate 54 comprises an adhesive which is attached to the bottom face 32 of the base 28. This adhesive attaches the mounting substrate 54 to the base 28 in a non-releasable manner. The bottom face 58 of the mounting substrate 54 also includes an adhesive, such as a pressure sensitive adhesive, which allows the apparatus 20 to be releasably adhered to the surface 60 near the patient.

In the preferred embodiment of the invention (FIGS. 1–8) the mounting substrate 54 is a double sided foam tape mounted to the bottom face 32 of the base 28. The mounting substrate 54 is a relatively flat rectangular member having an outer periphery, but may have any shape. The removable backing 62, releasably applied to the bottom face 58 of the mounting substrate 54, protects the adhesive so that the apparatus 20 can be packaged without sticking to any other substance. The removable backing 62 is mounted to the adhesive coating on the bottom face 58 of mounting substrate 54. The periphery of the backing 62 is larger than the periphery of the mounting substrate 54. This prevents the adhesive coating of the bottom face 58 of mounting substrate from coming into contact with another surface prior to the use of the apparatus 20. A side or corner of the removable backing 62 may be folded to facilitate grasping by a single gloved hand provided that the mounting substrate 54 is prevented from contacting other surfaces.

The needle sheath carrier 64 of the kit 20 extends from the base 28 and is at least partially attached to the base along one edge. In the primary embodiment of the present invention in FIGS. 1–8, the sheath carrier 64 includes top and bottom faces 66, 68 with a portion of the top face 66 of the sheath carrier 64 adhered to a part of the bottom face 32 of the base 28. The sheath carrier 64 also includes perforations 70 to allow for the separation of the sheath carrier 64 from the remainder of the apparatus 20. In the primary embodiment, the perforations 70 extend in a line from the proximal edge of the sheath carrier 64 to its distal edge in a direction parallel to the edge of the base 28 to which the sheath carrier is attached.

Disposed on the top face 66 of the sheath carrier 64 is the adhesive 72 for holding the I.V. needle sheath 26. This adhesive may be a gum, glue, foam adhesive or other adhesive substance suitable to hold, in a secure fashion, the sheath 26 during removal of an I.V. needle 22 and catheter 24 from the sheath and reinsertion of the I.V. needle 22 to the sheath. Prior to removal of the I.V. needle 22 and catheter 24 the sheath 26 is adhered to the adhesive 72 to facilitate removal of the I.V. needle 22 and catheter 24, and also for reinsertion of the contaminated I.V. needle with one gloved hand.

Figure 9:
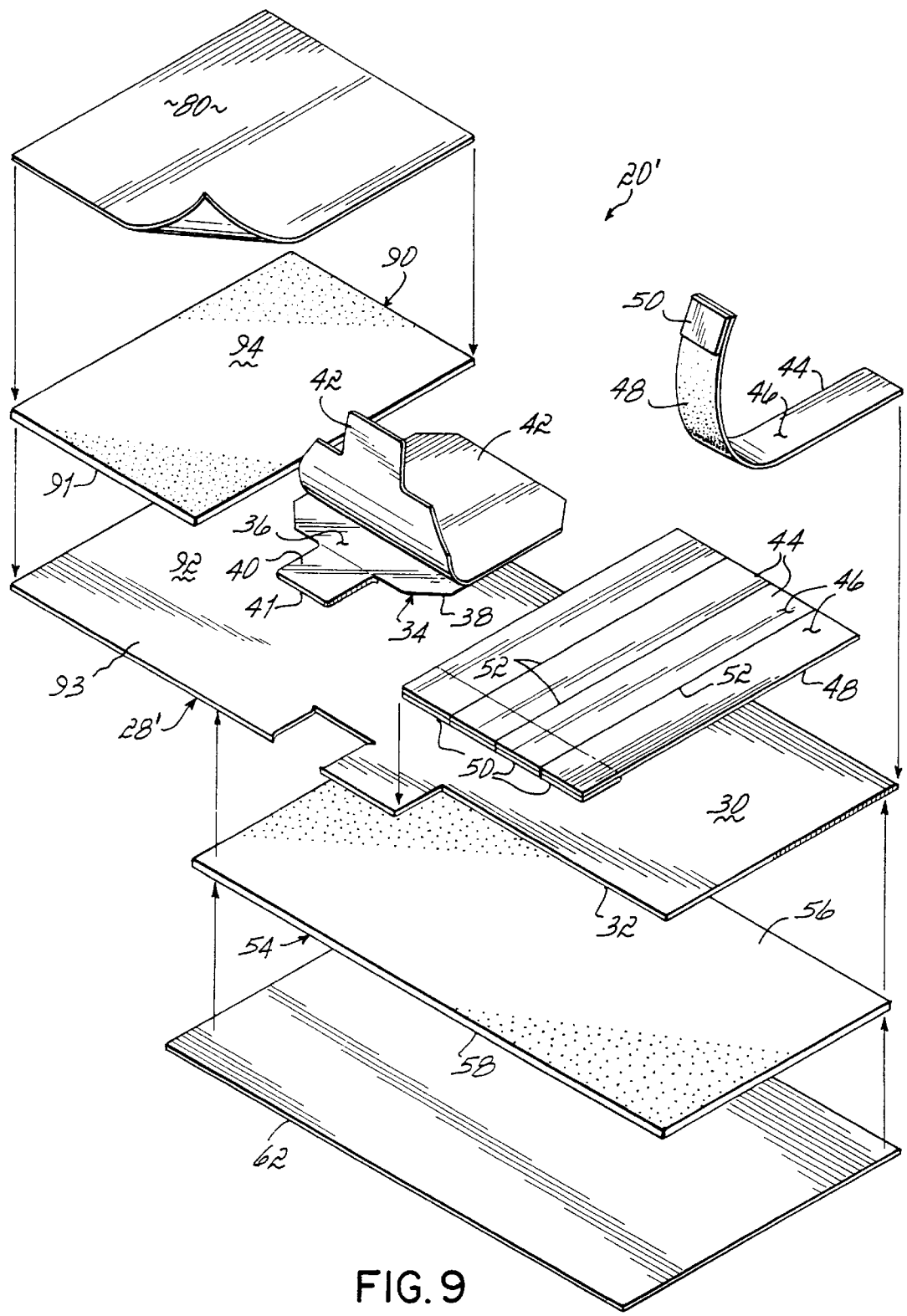
FIG. 9 is an exploded perspective view of an alternate embodiment of the kit.

In an alternate embodiment, a kit 20 is depicted in FIG. 9.

An adhesive substrate 90 may comprise a two-sided adhesive having top and bottom faces. This adhesive substrate 90 is analogous to the carrier 64 of the embodiment shown in FIG. 1. The bottom face 91 of the adhesive substrate 90 comprises an adhesive which adheres to the top face 92 of the extended end 93 of the base carrier 28' (which functions as the sheath carrier) in a non-releasable fashion. It will thus be appreciated that the base carrier 32' extends longitudinally throughout the kit to carry the disposable needle sheath and needle. The top face 94 of the adhesive holder 90 is an adhesive surface to which the sheath 26 containing needle 22 and catheter 24 may be adhered. The adhesive holder 90 is seen to consist of a rectangular member having an outer periphery. Moreover, in this embodiment the sheath carrier 93 is an integral part of the base carrier 28. In the embodiment of FIGS. 1–8, of course, the carrier 64 is a separate extension of the base 28. FIG. 9 shows the use of the single piece base 28' and the integral sheath carrier 93. Note that similar features of FIG. 9, as to those in FIGS. 1–8, are sometimes identified with a similar "primed" number.

Referring back to FIG. 1 in the primary embodiment, a removable cover 80 is releasably applied to the adhesive 72. The removable cover 80 is seen to have an outer periphery which is rectangularly shaped but may have any configuration. The cover 80 has an outer periphery which effectively covers the periphery of the adhesive 72 to prevent it from contacting any other surface prior to use of the kit 20. If desired a side of the removable cover 80 is folded to facilitate grasping by a single gloved hand. In the alternate embodiment depicted in FIG. 9, the removable cover 80 is releasably adhered to the top adhesive face 94 of the adhesive holder 90.

While the kit 20 described herein may be made in many different sizes, a kit 20, of particular usefulness is about six and three quarter inches in length, and 3 inches wide. The tape strips 44 are each about ½ inch wide and 3 inches long while the wound barrier 34 is about 1¾ inches wide and about 1–2 inches long to the tip of its tab 40. The sheath carrier 64 is about 2 inches long by about 3 inches wide. Moreover, in a preferred embodiment the following materials are useful, but others could be substituted. Preferably by way of example, the base carrier sheet 30 is an 83# liner, the mounting substrate 54 is 0.125 inch white foam adhesive, the under liner or backing is an 83# liner, the sheath carrier 64 is a 2 mil white polyester with pressure sensitive adhesive 72 as its top surface and its removable cover 80 is a 50# liner. A ½ inch unfolded tab 42 is disposed at the side for removing the site dressing (wound barrier film 34) and tape strips 34 may be of any suitable and well known material, the wound barrier 34 being preferably a very thin flexible, transparent film 34.

In use, as depicted in FIGS. 4–8, the kit 20 (or kit 20') is removed from its package (not shown—can be any encapsulating material) and the backing 62 on the bottom face 58 of the mounting substrate 54 is removed. The user grasps the backing 62 along an edge of its periphery extending beyond the periphery of the mounting substrate 54 to facilitate its removal. The exposed adhesive bottom face 58 of the mounting substrate 54 is then applied to any convenient and appropriate surface 60 near the procedure, for example to the bed clothes, sheets, bed rail, cabinet or other objects that reside in the area. Thereafter the technician, with gloved hands, can continue with the use of the kit, the sterilization of the site and the I.V. insertion procedure.

Figure 4:
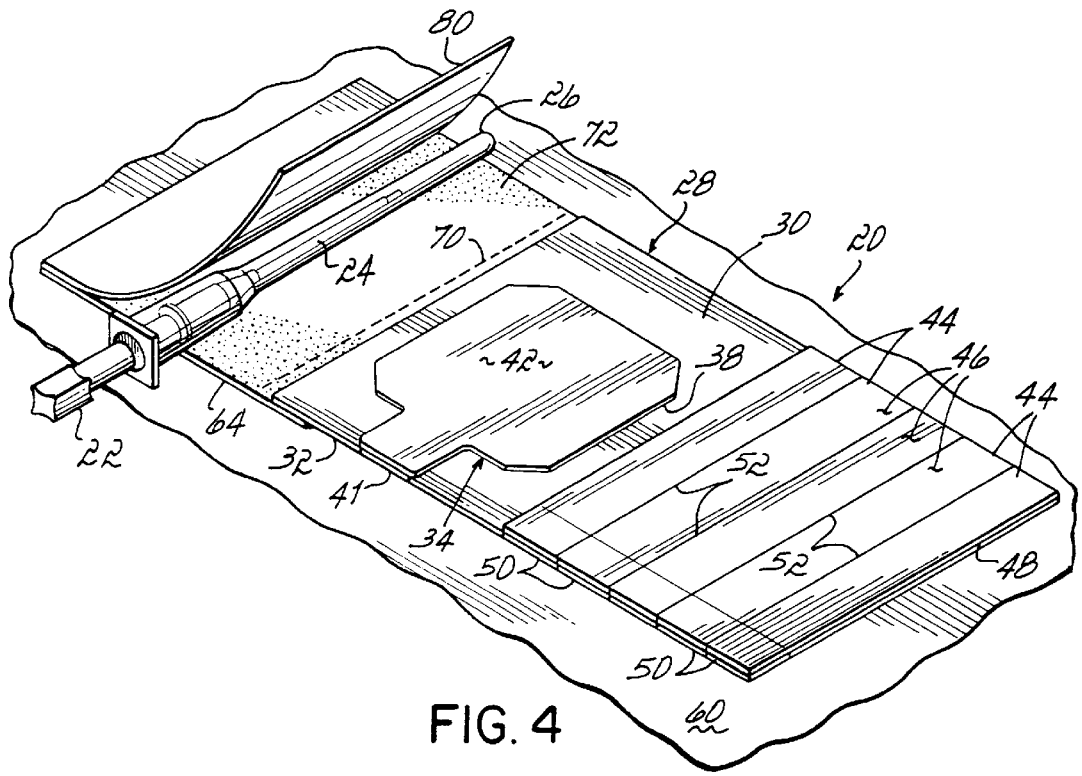
FIG. 4 is a perspective view of the kit illustrating the peel away cover and adhesive I.V. needle holder.
Figure 5:
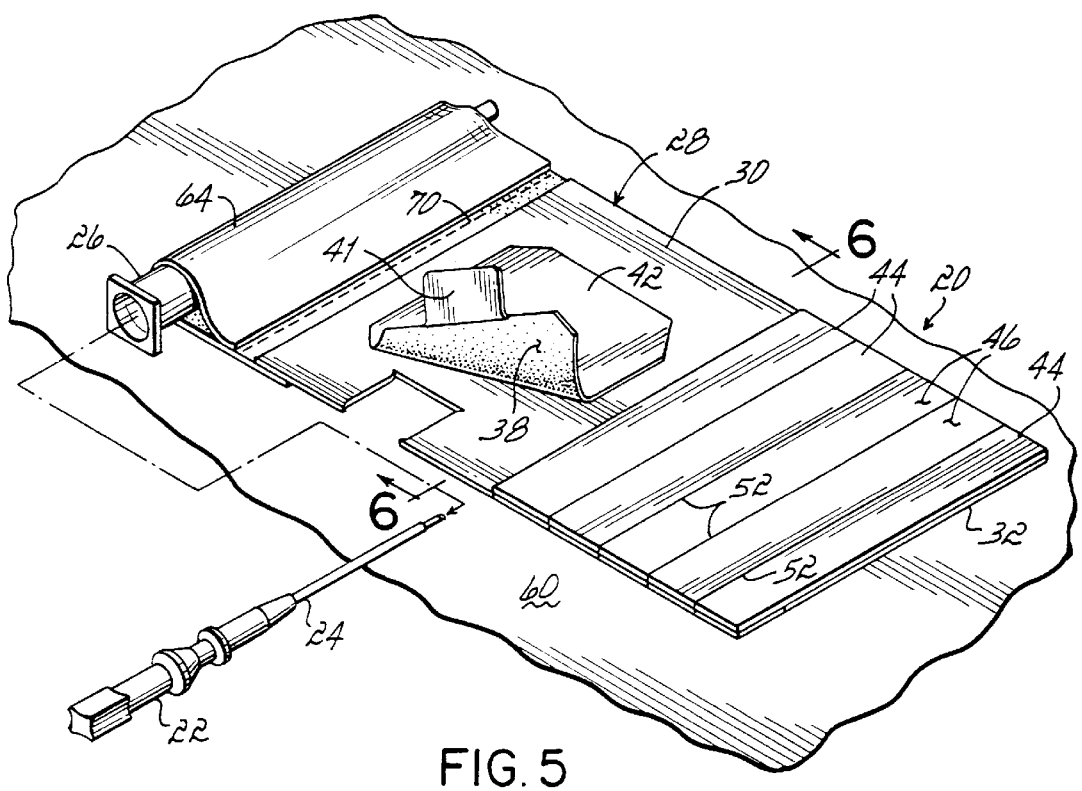
FIG. 5 is a perspective view of the kit further illustrating the releasably adhered wound barrier and adhesive I.V. needle holder.
Figure 6:
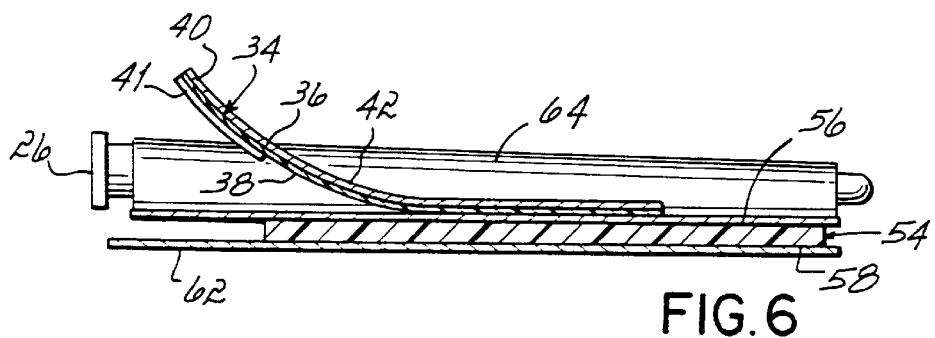
FIG. 6 is a cross-sectional view of the kit taken along lines 6—6 of FIG. 5.
Figure 7:
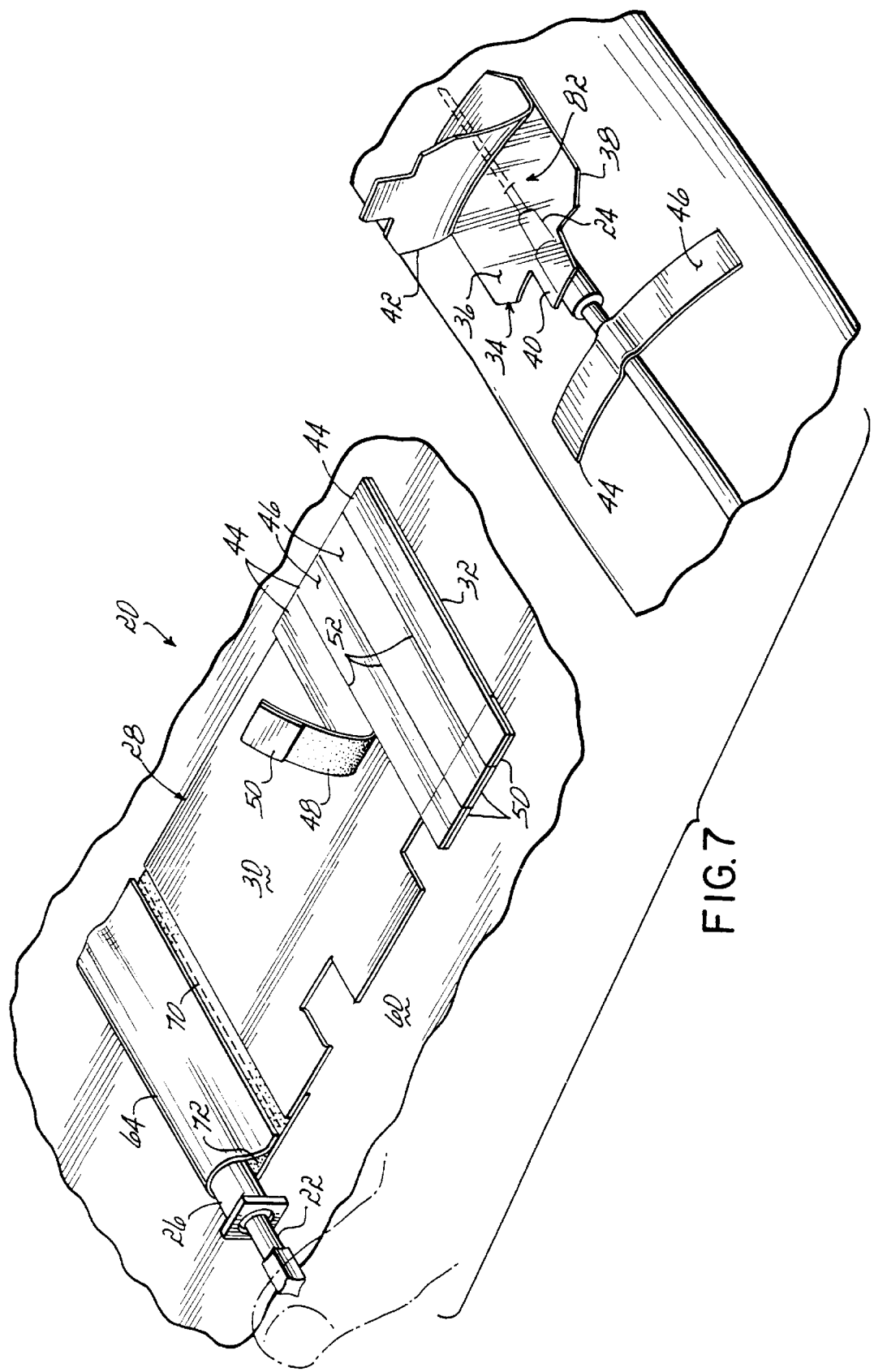
FIG. 7 is a perspective view of the kit illustrating the one handed reinsertion of a contaminated needle into a sheath, the peel away carrier and clear wound barrier, and the removable tape strips.

Referring to FIGS. 4 and 5, once a site on a patient has been prepared for the insertion of a catheter 24, the releasable cover 80 disposed above the adhesive 72 (94) is removed by a user grasping the cover along an edge of its periphery extending beyond the periphery of the adhesive holder. Once the cover 80 is removed, the adhesive 72 (or 94) disposed on the sheath carrier 64 (90) is exposed. Prior to the insertion of the needle 22 and catheter 24 into the patient, the sheath 26 housing the needle and catheter is placed on the adhesive 72 (94) of the kit 20, 20' and is thereby adhered to the sheath carrier 64. The top face 66 of the adhesive carrier 64 (90) including the adhesive 72 (94) is then folded around the sheath 26 and over the top of itself in order to secure the sheath to the kit 20, 20'. As the adhesive 72 and sheath carrier 64 (kit 20) are folded over the sheath 26, an open end of the sheath is left exposed to allow for removal of the catheter 24 and needle 22 prior to their use, and reinsertion of the needle following its use. Referring to FIGS. 5 and 7, the needle 22 and catheter 24 are then removed from the sheath 26. The needle is inserted and then removed, leaving the catheter in place, held by a thumb. After the needle 22 has been extracted from the patient the technician may keep pressure on the I.V. wound site 82 with the hand to prevent the catheter 24 from dislodging while using the other gloved hand to reinsert the contaminated needle into its sheath 26, which is adhered to the adhesive 72 of the kit 20. Of course, in a typical needle/sheath construction complimentary components are used to "snap" the needle 22 securely into the sheath 26 and hold the needle securely in the sheath.

It will be appreciated that the fold over of carrier 90 in kit 20' may be delayed until the wound barrier and tape strips are used.

Following reinsertion of the needle 22 into the sheath 26, and while the technician holds the catheter 24 in place at the wound site 82 with one hand, he or she may reach to the kit 20, 20' with their other hand to remove the releasably adhered wound barrier 34 to place over the catheter at the wound site. The removal of this wound barrier 34 is facilitated by the base tab 41 disposed on the bottom face 38 of the wound barrier 34, the protruding tab 40 of the wound barrier and the carrier 42 disposed on the top face 36 of the wound barrier. The technician grasps the tabs 40, 41 with said one hand to release the wound barrier 34 and carrier 42 from the base 28. The wound barrier 34 and carrier 42 are then applied to the skin surface of the patient over the wound site 82 and are adhered thereto by the adhesive bottom face 38 of the wound barrier. Following the application of the wound barrier 34 to the wound site 82 the carrier 42 is separated from the wound barrier 34 exposing the clear, flexible film of the wound barrier which facilitates observation of the wound site by the technician and allows for motion by the patient without risk of the wound barrier loosening and the catheter 24 dislodging.

Once the wound barrier 34 has been applied to the wound site 82, the adhesive tape strips 44 can be sequentially removed from the kit 20 with the same single gloved hand for further securing the wound barrier 34 and catheter 24 as required. This operation is illustrated in FIG. 7 where one tape strip is shown in place over the I.V. tubing. It will be appreciated that the other tapes 44 can be applied before or after the tubing is taped in a typical orientation, such as in a butterfly or crisscross position (not shown) to directly further secure the catheter 24 and all with one hand. Preferably, assuming a right-handed technician, the left thumb (not shown) is used to pressure the blood vessel and/or catheter to hold the catheter in place and/or control the blood flow until the procedure is complete. The removal of these tape strips 44 is facilitated by the technician grasping the tab 50 disposed on the bottom face 48 of the tape strips 44.

Figure 8:
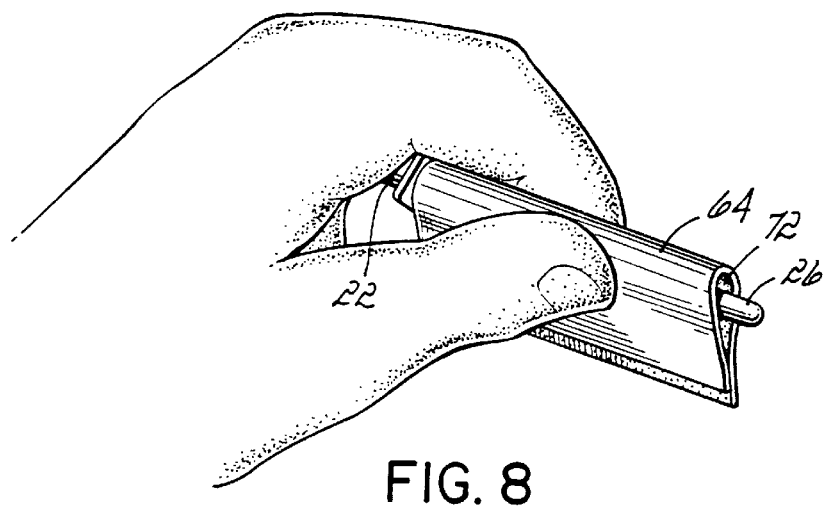
FIG. 8 is a perspective view of the separated adhesive I.V. needle holder and adhesive carrier of the present invention folded over for disposal of a contaminated needle.
Figure 10:
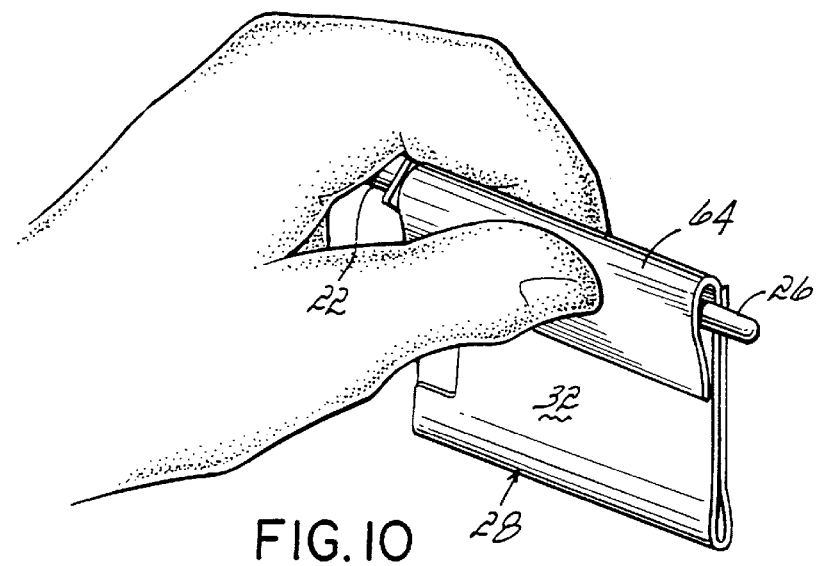
FIG. 10 is a perspective view similar to that of FIG. 8 but with reference to the apparatus of FIG. 9.

Referring now to FIG. 8, after securing the catheter 24 to the patient, the adhesive sheath carrier 64 having an adhesive 72 holding the sheath 26 containing contaminated needle 22 may be separated from the kit 20 along the perforations 70 included on one edge of the adhesive carrier. The needle 22, sheath 26, and adhesive carrier 64 with adhesive 72 may thus be safely disposed without risk of contamination, infection or injury to the technician or others. The remainder of the kit 20 may then be removed from the surface to which they are adhered and disposed of. It will be appreciated that the ability to sever the sheath carrier 64 from the remainder of the kit 20 is advantageous in reducing the volume of material to be disposed of in the typical hazardous waste/sharps disposal unit, as opposed to the alternate embodiment. Of kit 20' Alternately, the needle 22 could be carefully removed from the sheath 26 and disposed of in a sharps unit, eliminating the disposal of the sheath carrier 64 or other material in the sharps unit. At this time, of course, both hands are again available for this removal and disposal operation since there is no recapping occurring. In the alternate embodiment, depicted in FIG. 10, the entire kit 20', including the needle sheath 26, may be removed from the surface to which it is adhered, and folded over for disposal in a sharps waste unit without the risk of contamination, infection or injury.

Figure 11:
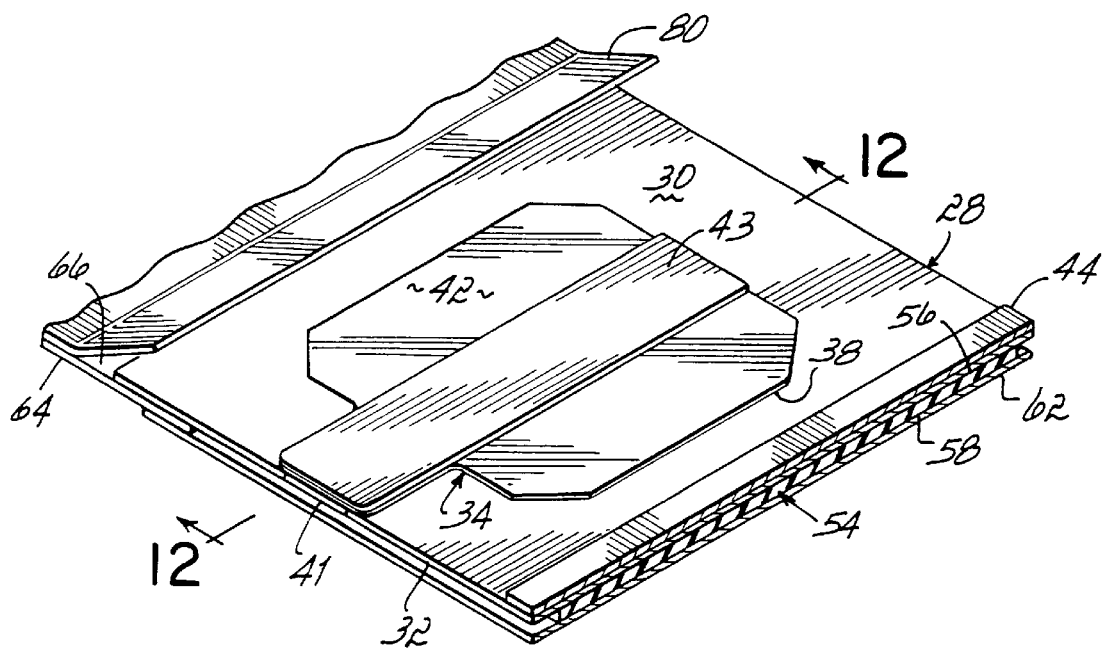
FIG. 11 is an illustration of optimal modification to the wound barrier of the apparatus shown in both FIGS. 1–8 and 9–10.
Figure 12:
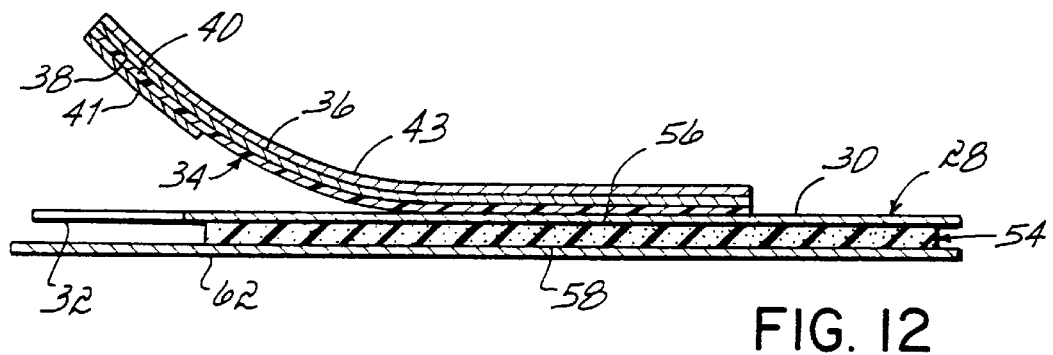
FIG. 12 is a cross-sectional view of the kit taken along lines 12—12 of FIG. 11.

Of course any suitable film 34, carrier 64, base carrier 28 and adhesives may be used in accordance with the invention and without departing from its scope. Finally, and with respect to FIGS. 11 and 12, to improve the operation of carrier 42 on film 34, another film or tape strip 43 can be placed on the carrier 42. This film or tape strip 43 tends to stiffen the carrier 42, and aid in its release following application of the wound barrier 34 to the patient. It should be noted that FIGS. 11 and 12 depict the modification of the carrier 42 of the wound barrier 34 to include the tape strip 43. All other components of the apparatus 20 are the same as depicted in FIGS. 1 and 9.

It should also be appreciated that the wound dressings, including the tapes 44 and wound barrier 34, can be of any suitable material, size or shape, and could be oriented differently on the base carrier 28 without departing from the scope of the invention. As an example, the tab 40 position of the wound barrier film 34 could extend from another edge, and it could be applied with the tab 40 reoriented 90 degrees from its position as shown in FIG. 7.

It will also be appreciated that the I.V. kits 20, 20' can be supplied with a needle 22 and catheter 24 within a sheath 26 already in place on the sheath carrier 64 as described herein. Thus, the invention may be prepared and sold as a complete kit with catheter 24 and needle 20, 20'.

Finally, it will be appreciated that the kit 20, 20' is useful for both one-handed or two-handed procedures, but is particularly useful and advantageous for one-handed use.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative apparatus and method, and illustrative example shown an described. Accordingly, departures may be made from such details without departing from the spirit or scope of applicants' general inventive concept.

What is claimed is:

1. A single-handed, I.V. catheter-securing apparatus for dressing an I.V. wound site and securing and shielding a needle for disposal following the insertion of an I.V. catheter into a subject, the apparatus comprising:

a base carrier having top and bottom faces;

wound dressings for securing said I.V. catheter to said subject, said dressings herein removably adhered to said top face of said base carrier;

a mounting substrate operably disposed on said bottom face for releasably attaching said apparatus to a surface; and a needle sheath carrier extending from said base carrier and having a needle sheath-attaching adhesive on a top face of said sheath carrier for holding a needle sheath thereon.

2. The apparatus of claim 1 wherein said wound dressings include a wound barrier film releasably mounted on said base carrier and comprising a wound barrier film carrier and an upper surface thereof, removable therefrom after application of said film of a wound site.

3. The apparatus of claim 2 further including a tape on an upper side of said wound barrier film carrier to facilitate removal of said carrier from said wound barrier film after mounting on a wound site.

4. The method of claim 3 further comprising the step of removing said wound barrier from top face of said base by grasping said tab of said wound barrier.

5. The method of claim 4 further comprising the step of applying said bottom face of said wound barrier to skin of said patient over said wound site.

6. The method of claim 5 further comprising the step of removing said releasably adhered carrier from said top face of said wound barrier.

7. The method of claim 6 further comprising the step of removing said tape strips from said top face of said base by grasping said tape strips by said tabs of said tape strips with said one hand.

8. The method of claim 7 further comprising the step of sequentially applying bottom faces of said plurality of tape strips to said patient to further secure said catheter to said I.V. wound site with said one hand.

9. The method of claim 8 further comprising the step of separating said adhesive carrier from said base along said perforation for disposal of said contaminated needle with a single gloved hand.

10. The apparatus of claim 1 wherein said wound dressings further comprise a wound barrier having a top face and an adhesive bottom face, said bottom face of said wound barrier releasably adhered to said top face of said base carrier.

11. The apparatus of claim 10 wherein said wound dressings further comprise a plurality of tape strips having top and bottom faces, said bottom faces of said tape strips releasably adhered to said top face of said base carrier.

12. The apparatus of claim 11 wherein said tape strips include tabs cut from said base to facilitate removal of said tape strips from said base carrier.

13. The apparatus of claim 12 wherein said tabs cut from said base are adhered to said bottom faces of said tape strips.

14. The apparatus of claim 13 wherein said tape strips are separated one from another by respective continuous cut lines.

15. The apparatus of claim 10 wherein said wound barrier includes a protruding tab adhered on a bottom face to a base tab cut from said base carrier to facilitate removal of said wound barrier from said base carrier.

16. The apparatus of claim 15 wherein said base tab on said wound barrier tab is adhered to said bottom face of said wound barrier.

17. The apparatus of claim 10 wherein said wound barrier further comprises a wound barrier carrier releasably adhered to said top face of said wound barrier and being removable from said base with said wound barrier to facilitate such removal.

18. The apparatus of claim 1 wherein said mounting substrate has top and bottom faces, said top face of said mounting substrate adhesively attached to said bottom face of said base carrier, and the bottom face of said mounting substrate further comprises an adhesive surface.

19. The apparatus of claim 18 wherein said mounting substrate further comprises a liner backing releasably adhered to said bottom face of said mounting substrate, whereby removal of said liner backing exposes adhesive surface of said bottom face of said mounting substrate for attaching said base carrier to a surface.

20. The apparatus of claim 1 wherein said sheath carrier is adhesively attached to the bottom surface of said base.

21. The apparatus of claim 20 wherein said sheath carrier is perforated to facilitate separation of said sheath carrier from said base carrier.

22. The apparatus of claim 20 wherein said sheath carrier further comprises top and bottom faces, at least a portion of said top face of said adhesive carrier being adhered to said bottom face of said base carrier by adhesive dispersed on the top surface of said sheath carrier.

23. The apparatus of claim 1 wherein said sheath carrier is an integral part of said base carrier.

24. The apparatus of claim 23 wherein said sheath carrier further includes a liner releasably adhered to a top face of said sheath carrier, whereby removal of said liner exposes adhesive on said top face of said sheath carrier to secure said sheath thereto.

25. The apparatus of claim 1 wherein said mounting substrate comprises a patterned adhesive.

26. The apparatus of claim 1 wherein said mounting substrate further comprises a two-sided foam adhesive member.

27. The apparatus of claim 1 further comprising a releasable cover releasably adhered to said sheath carrier, whereby removal of said cover exposes adhesive on the surface of said sheath carrier in securing a needle sheath thereto.

28. A method of securing an I.V. catheter to a subject, said method comprising the steps of:
providing an I.V. catheter-securing apparatus comprising a base having top and bottom faces, a wound barrier having top and bottom faces, said bottom face of said wound barrier releasably adhered to said top face of said base, a plurality of tape strips releasably adhered to said top face of said base, a mounting substrate having top and bottom faces for releasably attaching said base to a surface, said top face of said mounting substrate adhered to said bottom face of said base, an adhesive needle sheath carrier extending from said base for safely disposing of a contaminated catheter needle, the method further comprising:
adhering said apparatus to an available surface;
attaching a sheath containing an I.V. needle and catheter to said adhesive disposed on said sheath carrier;
inserting said I.V. needle and I.V. catheter into a patient at a wound site;
removing said I.V. needle from said patient;
replacing said I.V. needle in said sheath; and
securing said catheter to said patient with said wound barrier and said tape strips.

29. A method as in claim 28 wherein the sheath carrier includes an adhesive with a releaseable cover thereon, the method comprising the further step of removing said cover prior to attaching said sheath to said adhesive of said sheath carrier.

30. A method as in claim 29, wherein said base includes top and bottom faces and a perforated edge between said base and said sheath carrier, the method including the steps of folding said sheath carrier over said sheath after said sheath is placed thereon.

31. The method of claim 30 including the further step of removing said sheath carrier from said base along said line of perforations after said I.V. needle is replaced in said sheath.

32. A method as in claim 31 wherein at least one of said cover removal, folding and sheath carrier removal steps are carried out with one hand.

33. A method as in claim 32 where all said cover removal, folding and sheat carrier removal steps are carried out with one hand.

34. A method as in claim 28 where said mounting substrate further comprises a backing releasably adhered to said bottom face of said mounting substrate and further including the step of removing said backing before adhering said apparatus to an available surface.

35. A method as in claim 34 wherein the wound barrier includes a tab cut from said base and a carrier including a tape on an upper side of said carrier, said carrier releasably adhered to said top face of said wound barrier, said method including the steps of covering said wound site with said wount barrier and removing said carrier therefrom.

36. A method as in claim 35 wherein said wound site covering step is carried out with one hand.

37. A method as in claim 28 wherein all said sheath attaching, needle removal, needle replacing and catheter securing steps are carried out with one hand.

38. A method as in claim 37 wherein all said sheath attaching, needle removal, needle replacing and catheter securing steps are carried out with the same hand, while another hand holds the inserted catheter at the wound site.

39. A method as in claim 28 wherein said sheath attaching step is carried out with one hand.

40. A method as in claim 28 wherein said needle removal step is carried out with one hand.

41. A method as in claim 28 wherein said needle replacing step is carried out with one hand.

42. A method as in claim 28 wherein said catheter securing step is carried out with one hand.

43. A kit for use in securing an I.V. catheter to a patient and for use in disposing of a used I.V. catheter needle, said kit comprising:

a base carrier having top and bottom faces;

wound dressings for use in securing said I.V. catheter to said patient, said wound dressings being removably adhered to said top face of said base carrier;

a first adhesive operably secured to said bottom face of said base carrier for releasably attaching said base carrier to a surface;

a needle sheath carrier extending from said base carrier, said needle sheath carrier having a top surface; and a second adhesive operably secured to said top surface of said needle sheath carrier for use in holding a needle sheath thereon.

44. The kit of claim 43 further comprising a substrate adhered to the bottom face of said base carrier, said first adhesive disposed on a bottom of said substrate, said first adhesive comprising a patterned adhesive.

45. The kit of claim 44 wherein said substrate is a foam adhesive member.

46. The kit of claim 45 further comprising a liner backing releasably adhered to the bottom of said first adhesive.

47. The kit of claim 43, wherein said needle sheath carrier and said base carrier form a unitary structure.

48. A method of inserting an I.V. catheter into a patient comprising the steps of:

attaching a base carrier to a surface proximate a patient said base carrier carrying a wound barrier;

adhesively attaching a needle, catheter and catheter sheath to said base carrier;

removing the needle and catheter from the catheter sheat and inserting said needle and catheter into a blood vessel of the patient;

removing the needle from the patient and leaving the catheter in place at a wound site; and reinserting the needle into said sheath.

49. A method as in claim 48 including the further step of applying said wound barrier to said wound site over said catheter with said one hand.

50. A method as in claim 49 wherein said base carrier carries a plurality of wound dressing tape strips including the step of removing at least one tape strip from said base carrier with said one hand and securing said catheter in place with said one hand.

51. A method as in claim 48 comprising the further step of bending a portion of said base carrier over said sheath to secure it in said base carrier.

52. A method as in claim 51 wherein said base carrier includes a sheath carrier portion and a non-sheath carrier portion, the two portions being severably connected, the method further comprising the step of tearing the base carrier into said two portions for disposal of said sheath carrier portion.

53. A method as in claim 48 including the step of removing a wound barrier film and film carrier from said base carrier and applying in said releasable film and carrier over at least a portion of said catheter at said wound site.

54. A method as in claim 53 including carrying out the removal and applying steps with one hand.

55. A method as in claim 48 including removing a plurality of tape strips from said base carrier with said one hand and applying them to secure a catheter in place with said one hand.

56. A method as in claim 55 including holding said catheter in place with said other hand during wound barrier and tape strip removal and application with said other hand.

57. A method of securing an I.V. catheter in place at a wound site and including the steps of:

attaching a base carrier to a surface proximate a patient;

adhesively attaching a needle and catheter sheath to said base carrier;

removing the needle and catheter from the sheath with one hand and inserting it into a blood vessel;

removing the needle, thereafter with a single hand, and leaving the catheter in place;

reinserting the needle into said sheath with said one hand;

removing a wound barrier film from said base carrier and applying said film to said wound site over said catheter with said one hand; and removing at least one tape strip from said base carrier with said one hand and securing said catheter in place with said one hand and with said tape strip.

58. A method as in claim 57 comprising the further step of bending a portion of said base carrier over said sheath to secure it.

59. A method as in claim 58 which said base carrier includes a sheath carrier and the method including the step of tearing the base carrier to sever said sheath therefrom for disposal.

60. A method as in claim 57 including removing a plurality of tape strips from said base carrier with said one hand and applying them to secure a catheter in place with said one hand.

61. A method as in claim 60 including holding said catheter in place with another hand during wound barrier and tape strip removal and application with said one hand.

62. A method as in claim 57 including the step of removing a wound barrier film and film carrier from said base carrier and applying said film and film carrier to said wound site.

63. A method for using an I.V. catheter-securing apparatus to secure an I.V. catheter to a subject and comprising the steps of:

unwrapping an I.V. catheter-securing apparatus comprising a base having top and bottom faces, a wound barrier having top and bottom faces, said bottom face of said wound barrier releasably adhered to said top face of said base, said wound barrier including a tab cut from said base and a carrier including a tape on an upper side of said carrier, said carrier releasably adhered to said top face of said wound barrier, a plurality of tape strips releasably adhered to said top face of said base, having precut tabs to facilitate removal from said base, a mounting substrate having top and bottom faces for releasably attaching said apparatus to a surface, said top face of said mounting substrate adhered to said bottom face of said base and said mounting substrate further comprising a backing releasably adhered to said bottom face of said mounting substrate, an adhesive needle sheath carrier extending from said base having top and bottom faces and a perforated edge, and an adhesive disposed on said top face of said sheath carrier for safely disposing of a contaminated catheter needle, and a cover releasably adhered to said adhesive; the method further comprising:

adhering said apparatus to an available surface;

removing said cover and attaching a sheath containing an I.V. needle and catheter to said adhesive disposed on said sheath carrier;

inserting said I.V. needle and I.V. catheter into a patient; and thereafter with one hand:

removing said I.V. needle from said patient;

replacing said I.V. needle in said sheath with one hand; and securing said catheter to said patient with said wound dressings with said one hand.

64. The method of claim 63 further comprising the step of folding said sheath carrier having said adhesive to secure said sheath therein, with an open end of said sheath exposed beyond one edge of said folded sheath carrier having said adhesive.

65. The method of claim 64 further comprising the step of removing said I.V. catheter and said I.V. needle from said sheath on said sheath carrier and inserting said I.V. catheter and said I.V. needle into said patient.

* * * * *

UNITED STATES PATENT AND TRADEMARK OFFICE
CERTIFICATE OF CORRECTION

PATENT NO. : 6,099,509
DATED : August 8, 2000
INVENTOR(S) : William S. Brown, Jr. and Benjamin C. Brown It is certified that error appears in the above-identified patent and that said Letters Patent is hereby corrected as shown below:

Column 2,
Line 67, replace "...adhesive tapes One of..." with -- ...adhesive tapes. One of... --.

Column 4,
Line 34, replace "one handed" with -- one-handed --.
Line 50, replace "...of a one embodiment..." with -- ...of one embodiment.... --.

Column 6,
Line 41, replace "...double sided" with -- double sided --.

Column 7,
Line 50, replace "...a kit 20, of particular..." with -- ...a kit 20 of particular... --.
Line 60, replace "under liner" with -- underliner --.

Column 8,
Line 41, replace "complimentary" with -- complementary --.

Column 9,
Line 27, replace "...to which they are...." with -- to which it is --.
Line 32, replace "...Of kit 20' Alternately..." with -- of kit 20. Alternately ... --.

Column 10,
Line 13, replace "...illustrative example shown an described." with -- ...illustrative example shown and described. --.
Line 37, replace "...said film of a wound site." with -- ...said film on a wound site --.

Column 12,
Line 35, replace "sheat" with -- sheath --.
Line 47, replace "wount" with -- wound --.

UNITED STATES PATENT AND TRADEMARK OFFICE
CERTIFICATE OF CORRECTION

PATENT NO. : 6,099,509
DATED : August 8, 2000
INVENTOR(S) : William S. Brown, Jr. and Benjamin C. Brown It is certified that error appears in the above-identified patent and that said Letters Patent is hereby corrected as shown below:

<u>Column 13,</u>
Line 26, replace "...patient said...." with -- patient, said... --.
Line 30, replace "sheat" with -- sheath --.
Line 55, replace "...applying in said releasable film..." with -- ...applying said releasable film... --.

Signed and Sealed this

Sixteenth Day of April, 2002

Attest:

JAMES E. ROGAN
*Attesting Officer*   *Director of the United States Patent and Trademark Office*